(12) United States Patent
Burgmeier et al.

(10) Patent No.: US 7,387,826 B2
(45) Date of Patent: Jun. 17, 2008

(54) MEDICAL DEVICE WITH VARYING PHYSICAL PROPERTIES AND METHOD FOR FORMING SAME

(75) Inventors: Robert Burgmeier, Plymouth, MN (US); Richard L. Goodin, Blaine, MN (US); Joseph Delaney, Jr., Minneapolis, MN (US); Larry Peterson, Champlin, MN (US)

(73) Assignee: Boston Scienitific Scimed, Inc., Maple Grove, MN (US)

( * ) Notice: Subject to any disclaimer, the term of this patent is extended or adjusted under 35 U.S.C. 154(b) by 868 days.

(21) Appl. No.: 10/772,477

(22) Filed: Feb. 5, 2004

(65) Prior Publication Data

US 2005/0142314 A1 Jun. 30, 2005

Related U.S. Application Data

(63) Continuation-in-part of application No. 10/749,821, filed on Dec. 31, 2003.

(51) Int. Cl.
*B29D 22/00* (2006.01)
*A61M 25/10* (2006.01)

(52) U.S. Cl. ............... 428/35.7; 428/36.9; 428/36.92; 604/264; 604/915; 604/96.01; 604/103.06

(58) Field of Classification Search ............... 427/2.1, 427/2.3; 600/435; 604/915, 912, 921; 428/35.7, 428/36.9, 36.7; 138/118, 137
See application file for complete search history.

(56) References Cited

U.S. PATENT DOCUMENTS

| | | | |
|---|---|---|---|
| 3,752,617 A * | 8/1973 | Burlis et al. ............. | 425/131.1 |
| 4,110,283 A | 8/1978 | Capelle ..................... | 507/90 |
| 4,276,250 A * | 6/1981 | Satchell et al. ............ | 264/167 |
| 4,490,421 A | 12/1984 | Levy ......................... | 428/35 |
| 4,663,471 A | 5/1987 | Shinohara et al. .......... | 556/411 |
| 4,722,344 A * | 2/1988 | Cambron et al. ........... | 600/435 |
| 4,762,946 A | 8/1988 | Ritter et al. ................ | 560/179 |
| 4,906,244 A | 3/1990 | Pinchuk et al. ............. | 606/194 |
| 4,950,239 A | 8/1990 | Gahara et al. .............. | 604/96 |
| 5,088,991 A | 2/1992 | Weldon ...................... | 604/280 |
| 5,096,848 A | 3/1992 | Kawamura ................. | 437/67 |

(Continued)

FOREIGN PATENT DOCUMENTS

EP 0 376 656 7/1990

(Continued)

OTHER PUBLICATIONS

T.L. St. Clair and H.D. Burks, "Thermoplastic/Melt-Processable Plyimides," NASA Conf. Pub. #2334 (1984) pp. 337-355.

(Continued)

*Primary Examiner*—D. Lawrence Tarazano
*Assistant Examiner*—Michele Jacobson
(74) *Attorney, Agent, or Firm*—Vidas, Arrett & Steinkraus

(57) ABSTRACT

A medical device in which a melt processed part has different crystallized properties at different locations. The part is formed of a polymer composition by inclusion a of polymer crystallization modifier in the composition making up at least a portion of such part, the amount of the polymer crystallization modifier is varied at different locations on the part in accordance with the desired difference in crystallization behavior.

21 Claims, 2 Drawing Sheets

U.S. PATENT DOCUMENTS

| | | | |
|---|---|---|---|
| 5,250,069 A | 10/1993 | Nobuyoshi et al. | 606/192 |
| 5,258,160 A * | 11/1993 | Utsumi et al. | 264/558 |
| 5,264,260 A | 11/1993 | Saab | 428/35.5 |
| 5,270,086 A | 12/1993 | Hamlin | 428/35.2 |
| 5,300,581 A | 4/1994 | Otawa et al. | 525/301 |
| 5,306,246 A * | 4/1994 | Sahatjian et al. | 604/96.01 |
| 5,308,342 A | 5/1994 | Sepetka et al. | 604/525 |
| 5,316,706 A * | 5/1994 | Muni et al. | 264/472 |
| 5,328,468 A | 7/1994 | Kaneko et al. | 604/96 |
| 5,330,428 A | 7/1994 | Wang et al. | 604/96 |
| 5,344,400 A | 9/1994 | Kaneko et al. | 604/96 |
| 5,500,180 A | 3/1996 | Anderson et al. | 264/532 |
| 5,516,565 A * | 5/1996 | Matsumoto | 428/35.7 |
| 5,556,383 A | 9/1996 | Wang et al. | 604/96 |
| 5,614,136 A | 3/1997 | Pepin et al. | |
| 5,797,877 A | 8/1998 | Hamilton et al. | 604/96 |
| 6,001,085 A * | 12/1999 | Lurie et al. | 604/524 |
| 6,030,405 A * | 2/2000 | Zarbatany et al. | 606/191 |
| 6,146,356 A | 11/2000 | Wang et al. | 604/96 |
| 6,242,063 B1 * | 6/2001 | Ferrera et al. | 428/35.2 |
| 6,254,949 B1 * | 7/2001 | Gluck et al. | 428/36.91 |
| 6,270,522 B1 | 8/2001 | Simhambhatla et al. | 623/11.1 |
| 6,284,333 B1 * | 9/2001 | Wang et al. | 428/35.5 |
| 6,319,454 B1 * | 11/2001 | Nakagawa et al. | 264/515 |
| 6,325,790 B1 * | 12/2001 | Trotta | 604/523 |
| 6,355,027 B1 * | 3/2002 | Le et al. | 604/525 |
| 6,358,227 B1 | 3/2002 | Ferrera et al. | 604/103.06 |
| 6,358,450 B1 * | 3/2002 | Sun | 264/178 R |
| 6,436,056 B1 | 8/2002 | Wang et al. | |
| 6,465,067 B1 * | 10/2002 | Wang et al. | 428/35.7 |
| 6,524,296 B1 * | 2/2003 | Beals | 604/500 |
| 6,524,299 B1 * | 2/2003 | Tran et al. | 604/523 |
| 6,552,123 B1 | 4/2003 | Katayama et al. | |
| 6,572,813 B1 | 6/2003 | Zhang et al. | 264/519 |
| 6,585,688 B2 | 7/2003 | Ferrera et al. | 604/96.01 |
| 6,596,296 B1 | 7/2003 | Nelson et al. | |
| 6,610,765 B1 | 8/2003 | Pfaendner et al. | 524/108 |
| 6,765,059 B2 * | 7/2004 | Corley | 525/66 |
| 6,905,743 B1 | 6/2005 | Chen et al. | |
| 7,104,979 B2 * | 9/2006 | Jansen et al. | 604/525 |
| 7,128,956 B2 * | 10/2006 | Wang et al. | 428/36.9 |
| 2001/0027310 A1 * | 10/2001 | Parisi et al. | 604/524 |
| 2002/0045017 A1 * | 4/2002 | Wang et al. | 428/35.2 |
| 2003/0054161 A1 | 3/2003 | Forte et al. | 428/332 |
| 2003/0148056 A1 | 8/2003 | Utz et al. | 428/43 |
| 2003/0152728 A1 | 8/2003 | Wang et al. | 428/36.9 |
| 2003/0167067 A1 | 9/2003 | Wang et al. | 606/192 |
| 2004/0181271 A1 * | 9/2004 | DeSimone et al. | 623/1.1 |
| 2004/0241364 A1 * | 12/2004 | Zihlmann | 428/35.7 |
| 2005/0043679 A1 * | 2/2005 | Devens et al. | 604/103.06 |
| 2005/0118370 A1 * | 6/2005 | Varma et al. | 428/35.7 |
| 2005/0233062 A1 * | 10/2005 | Hossainy et al. | 427/2.1 |

FOREIGN PATENT DOCUMENTS

| | | |
|---|---|---|
| JP | 2003062081 A | 3/2003 |
| WO | 94/21726 | 9/1994 |
| WO | WO 00/01420 | 1/2000 |
| WO | WO 03/051421 | 6/2003 |

OTHER PUBLICATIONS

U.S. Appl. No. 10/617428, filed Jul. 10, 2003, Schewe et al.
U.S. Appl. No. 10/749821, filed Dec. 31, 2003, Burgmeier et al.

* cited by examiner

MEDICAL DEVICE WITH VARYING PHYSICAL PROPERTIES AND METHOD FOR FORMING SAME

CROSS-REFERENCE TO RELATED APPLICATIONS

This application is a Continuation in Part application of Ser. No. 10/749,821, filed Dec. 31, 2003.

BACKGROUND OF THE INVENTION

Various medical devices, such as catheters, tubes, balloons, stents and the like, are known to have physical performance requirements which change at particular points, or ranges of area or length. For instance, catheters typically need to be soft and flexible toward the distal end while at the same time becoming much more rigid and kink resistant proximally in order to effectively transmit torque and crossing forces from their proximal ends to the distal tip.

Medical devices comprising catheter balloons are used in an increasingly widening variety of applications including vascular dilatation, stent delivery, drug delivery, delivery and operation of sensors and surgical devices such as blades, and the like. The desired physical property profile for the balloons used in these devices vary according to the specific application, but for many applications a high strength robust balloon is necessary and good softness and trackability properties are highly desirable.

Commercial catheter balloons have been formed of a wide variety of polymeric materials, including PET, nylons, polyurethanes, polyolefins, and various block copolymer thermoplastic elastomers.

U.S. Pat. No. 4,490,421, Levy, and U.S. Pat. No. 5,264,260, Saab, describe PET balloons. U.S. Pat. No. 4,906,244, Pinchuk et al, and U.S. Pat. No. 5,328,468, Kaneko, describe polyamide balloons. U.S. Pat. No. 4,950,239, Gahara, and U.S. Pat. No. 5,500,180, Anderson et al describe balloons made from polyurethane block copolymers. U.S. Pat. No. 5,556,383, Wang et al and U.S. Pat. No. 6,146,356, Wang et al, describes balloons made from polyether-block-amide copolymers and polyester-block-ether copolymers. U.S. Pat. No. 6,270,522, Simhambhatla, et al, describes balloons made from polyester-block-ether copolymers of high flexural modulus. U.S. Pat. No. 5,344,400, Kaneko, describes balloons made from polyarylene sulfide. All of these balloons are produced from extruded tubing of the polymeric material by a blow-forming radial expansion process. U.S. Pat. No. 5,250,069, Nobuyoshi et al, U.S. Pat. No. 5,797,877, Hamilton et al, and U.S. Pat. No. 5,270,086, Hamlin, mention still further materials which may be used to make such balloons.

It has been found that polymers with a high content of butylene terephthalate can crystallize so extensively from an extrusion melt that balloon formation from an extruded parison is very difficult, if possible. A solution to this problem, taught in U.S. Pat. No. 6,465,067, Wang et al, is to add boric acid to the polymer composition.

In commonly owned copending U.S. application Ser. No. 10/055,747, medical devices formed of thermoplastic polymers containing chain extension additives which increase polymer molecular weight are described.

In commonly owned copending U.S. application Ser. No. 10/087,653, filed Feb. 28, 2002, incorporated herein by reference, it is disclosed that improved balloon properties can be obtained by controlling the parison extrusion in a manner which restricts the elongation of the parison material in the longitudinal direction. The application discloses that decreasing the gap between the extrusion head and the cooling bath tank can lower parison elongation by shortening the quench time.

In commonly owned copending U.S. application Ser. No. 10/617,428, filed Jul. 10, 2003, it is taught that varying the cooling tank gap during an extrusion can provide a catheter tube or balloon parison which has variable properties along its length.

In a balloon catheter, heat welded balloon-to-tube bonds, typically provided by laser heating, are commonly used for their high reliability. However, heat welded bonds provide a new problem, the melted or softened regions of the joined parts will often resolidify relatively slowly, allowing crystallization to develop with consequent increased stiffness. At the distal end of the catheter where the balloon is typically bonded to the catheter inner tube, the increased crystallinity in the bond can adversely affect the desired softness and trackability and of the catheter tip. Selecting a slow crystallizing polymer for the balloon material is usually not a suitable option since balloon material selection and processing steps are typically directed to maximizing balloon wall strength and hence providing a high degree of crystallization.

At the same time the catheter distal outer tube near the site, where it is bonded to the proximal waist of the balloon, often is subjected to very high tensile stress when the balloon is collapsed after use and is being withdrawn into a guide catheter or a protective sleeve. In some cases, particularly with larger balloons, the catheter shaft immediately proximal of the balloon may begin to yield before the balloon is successfully withdrawn. Consequently the tensile strength of the catheter outer can limit the minimum guide catheter or sleeve diameter which may be used with the catheter.

SUMMARY OF THE INVENTION

The present invention is directed to medical devices that are formed of thermoplastic material or materials, and to methods of forming such devices. In particular it is directed to such devices in which a melt processed part desirably has different crystallizing properties at different locations. In accordance with the invention the part is formed of a polymer composition by inclusion a of polymer crystallization modifier in the composition making up at least a portion of such part, the amount of the polymer crystallization modifier being varied in the part in accordance with the desired difference in crystallization behavior.

In one embodiment a catheter shaft is prepared by a technique in which the extruded tubing composition has a varying content of crystallization modifier along the tubing length. The catheter shaft may be an outer shaft in which the composition extruded to form the tubing distal end comprises a crystallization enhancer to locally increase the distal end tensile strength.

In another embodiment a tubular balloon parison is extruded with a composition which varies in composition by localized inclusion of a crystallization inhibitor. The portion of the parison which forms the distal waist of the balloon may be provided with such inhibitor in order to reduce the rigidity which develops upon heat welding of the balloon to the distal inner tube of the catheter.

Further aspects of the invention are described in the following detailed description of the invention or in the claims.

DETAILED DESCRIPTION OF THE INVENTION

Figure 1:
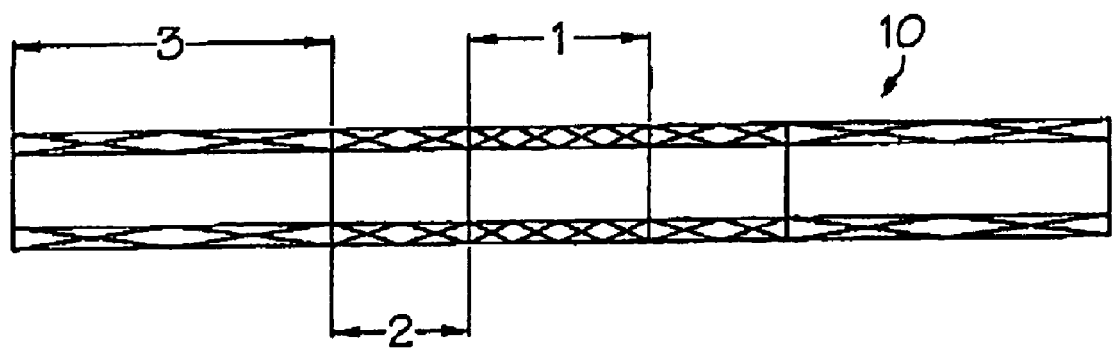
FIG. 1 is a schematic diagram of an extruded tubular balloon parison prepared in accordance with one embodiment of the present invention.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The medical device parts to which the invention may be applied include tubes, cannulae, catheter shafts, balloons and parisons therefor, stents, connectors, leads, or parts of any such devices. The part may be the entire device or a discretely formed portion thereof It may be a layer of a laminate article.

The medical device part is formed of melt processed polymer material. The polymer material is formed of a polymer material composition which comprises a thermoplastic polymer or mixture thereof In at least a portion of the part, the polymer composition further comprises a crystallization modifier. From a first portion of the inventive part to a second portion thereof, the composition is varied in the amount of crystallization modifier employed therein.

The invention may be used with any known semi-crystalline thermoplastic materials. Such materials may include olefin polymers and copolymers, acrylic, styrenic and vinyl polymers (e.g. poly(vinyl chloride)) and copolymers; polyethers; polyurethanes; polyesters and copolyesters; polycarbonates; thermoplastic elastomers; silicone-polycarbonate copolymers; polyamides; thermoplastic polyimides; liquid crystal polymers; ABS (acrylonitrile butadiene styrene); ANS (acrylonitrile styrene); Delrin polyacetal; PEI (polyetherimide); polyetheretherketone (PEEK) and polyether sulfone (PES). Film forming polymers may be used.

Olefin polymers and copolymers include irradiated polyethylene, polypropylene, ultra-high molecular weight polyolefins, low, linear low, medium and high density polyethylenes; polypropylenes; poly(ethylene vinyl acetate) (EVA); poly(ethylene vinyl alcohol) (EVOH) and EVA/EVOH terpolymers; ethylene-butylene-styrene block copolymers blended with low molecular weight polystyrene and, optionally, polypropylene, and similar compositions substituting butadiene or isoprene in place of the ethylene and butylene, and olefin ionomers (copolymers of olefin monomers and a metal salt of an olefinic acid, such as (meth)acrylic acid, succinic acid, maleic acid or fumaric acid).

Orientable polyesters, especially polyethylene terephthalate (PET), are among materials for forming catheter balloons. Suitable PET polymers have an initial intrinsic viscosity of at least 0.5, for instance, 0.6-1.3. Other high strength polyester materials, such as poly(ethylene napthalenedicarboxylate) (PEN), polytrimethylene terephthalate (PTT) and poly(butylene terephthalate) (PBT) may also be used. Polyester copolymers may also be employed, for instance, the random copolymers made from dimethyl terephthalate, dimethyl isophthalate and ethylene glycol described in U.S. Pat. No. 5,330,428, Wang et al.

Examples of polyamides which may be used include nylon 6, nylon 64, nylon 66, nylon 610, nylon 610, nylon 612, nylon 46, nylon 9, nylon 10, nylon 11, nylon 12, and mixtures thereof.

The medical device article may be formed of polyurethanes such as Tecothane® from Thermedics. Tecothane® is a thermoplastic, aromatic, polyether polyurethane synthesized from methylene diisocyanate (MDI), polytetramethylene ether glycol (PTMEG) and 1,4 butanediol chain extender. Tecothane® 1065D and 1075D are examples. Other polyurethanes which have been used are Isoplast® 301, a high strength engineering thermoplastic polyurethane, and Pellethane® 2363-75D, both sold by Dow Chemical Co. References illustrating polyurethane balloon materials include U.S. Pat. No. 4,950,239, to Gahara, U.S. Pat. No. 5,500,180 to Anderson et al, U.S. Pat. No. 6,146,356 to Wang, et al., and U.S. Pat. No. 6,572,813, to Zhang, et al.

Articles of the invention may be also made of polyamide/polyether block copolymers. The polyamide/polyether block copolymers are commonly identified by the acronym PEBA (polyether block amide). The polyamide and polyether segments of these block copolymers may be linked through amide linkages, however, most preferred are ester linked segmented polymers, i.e. polyamide/polyether polyesters. Such polyamide/polyether/polyester block copolymers are made by a molten state polycondensation reaction of a dicarboxylic polyamide and a polyether diol. The result is a short chain polyester made up of blocks of polyamide and polyether.

Polyamide/polyether polyesters are sold commercially under the Pebax® trademark by Elf Atochem North America, Inc., Philadelphia Pa. Examples of suitable commercially available polymers are the Pebax® 33 series polymers with hardness 60 and above, Shore D scale, especially Pebax® 6333, 7033 and 7233. These polymers are made up of nylon 12 segments and poly(tetramethylene ether) segments.

It is also possible to utilize polyester/polyether segmented block copolymers and obtain similar balloon properties. Such polymers are made up of at least two polyester and at least two polyether segments. The polyether segments are the same as previously described for the polyamide/polyether block copolymers useful in the invention. The polyester segments are polyesters of an aromatic dicarboxylic acid and a two to four carbon diol. The polyether segments of the polyester/polyether segmented block copolymers are aliphatic polyethers having at least 2 and no more than 10 linear saturated aliphatic carbon atoms between ether linkages. More preferably the ether segments have 4-6 carbons between ether linkages, and most preferably they are poly(tetramethylene ether) segments. Examples of other polyethers which may be employed in place of the preferred tetramethylene ether segments include polyethylene glycol, polypropylene glycol, poly(pentamethylene ether) and poly(hexamethylene ether). The hydrocarbon portions of the polyether may be optionally branched. An example is the polyether of 2-ethylhexane diol. Generally such branches will contain no more than two carbon atoms. The molecular weight of the polyether segments is suitably between about 400 and 2,500, preferably between 650 and 1000.

The polyester segments may be polyesters of an aromatic dicarboxylic acid and a two to four carbon diol. Suitable dicarboxylic acids used to prepare the polyester segments of the polyester/polyether block copolymers are ortho-, meta- or para-phthalic acid, napthalenedicarboxylic acid or meta-terphenyl-4,4'-dicarboxylic acids. Preferred polyester/polyether block copolymers are poly(butylene terephthalate)-block-poly(tetramethylene oxide) polymers such as Arnitel® EM 740, sold by DSM Engineering Plastics, and Hytrel® polymers, sold by DuPont, such as Hytrel 8230.

Examples of thermoplastic polyimides are described in T. L. St. Clair and H. D. Burks, "Thermoplastic/Melt-Processable Polyimides," NASA Conf. Pub. #2334 (1984), pp. 337-355. A suitable thermoplastic polyimide is described in U.S. Pat. No. 5,096,848 and is available commercially under the tradename Aurum® from Mitsui Toatsu Chemicals, Inc., of Tokyo, Japan.

Examples of liquid crystal polymers include the products Vectra® from Hoechst Celanese; Rodrun® from Unitika; LX and HX series polymers and Zenite™ polymers from DuPont; Sumikosuper™ and Ekonol™ from Sumitomo Chemical; Granlar™ from Grandmont; and Xydar® from Amoco. Suitably the liquid crystal polymer materials are blended with another thermoplastic polymer such as PET, nylon 12, or a block copolymer such as Pebax® 7033 or 7233 or Arintel(D EM 740 or Hytrel 8230. In some cases the liquid crystal polymer may be present in a blend as fibers dispersed in a matrix.

Physical blends and copolymers of such materials may also be used.

Crystallization modifiers are known which enhance crystallization, for instance by providing more effective nucleation sites, increasing crystallization rate or by other mechanisms. Other crystallization modifiers inhibit crystallization, for instance by tying up nucleating sites or terminating crystal propagation, or by some other mechanism. Either way, the invention contemplates that the polymer modification can be introduced locally for instance in the course of extruding, injection molding, or the like.

The inhibitory effects of certain additives toward crystallization can be explained as a result of the additive's ability to disrupt the lattice order when adsorbed to the surface of the crystal. Typically, a good inhibitor of nucleation and/or of crystal growth will possess some functional groups that are identical to those of the solute of interest, which allows the agent to hydrogen bond to the material of interest, much as would otherwise happen during the normal processes of crystallization and nucleation. However, despite the chemical and geometric structural similarities between the substrate and the inhibitor, the typical inhibitor possesses additional functional groups which interfere with the geometric patterns critical crystal formation. By hydrogen bonding to the surface of the solute as it begins to crystallize, the inhibitor impedes subsequent crystallization. Some modifications made to "tailor-made" inhibitors include the use of stereoisomers, or use of analogs of the solute of interest, e.g. hydroxyl groups replacing amines, acids for amides, etc. The result is a different geometry to the hydrogen bonding taking place, and an overall loss in interatomic bond energy.

Very active inorganic admixtures, characterized by a strong tendency to form coordination complexes, decrease the nucleation rate. One explanation is that heteroclusters are formed in the bulk solution with the center formed by an active ion, which results in redistributing of the solute forming supersaturation to these heteroclusters so that supersaturation is effectively decreased. A good example of this phenomenon is the PE additive lithium [(bis)trifluoromethanesulfonate imide]. The large, bulky anion is thought to be responsible for the suppression of crystallization.

Table 1 provides examples of various types of polymers and crystallization inhibitors which may be utilized therewith:

TABLE 1

| Polymer | Inhibitors |
| --- | --- |
| Poly(ethylene oxide) | Acrylamide polymers such as polyacrylamide and poly(N,N'-dimethyl acrylamide); Lithium (bis)trifluoromethanesulfonate imide; Ceramic powders (nanometer size); Perfluorinated polyphosphazine; Electrolyte salts (e.g. LiAlO$_2$; LiClO$_4$) |
| Polysaccharides | Lactose |
| Polyesters (e.g. PET); Poly(ester-ether) block copolymers; Poly(ester—ester) block copolymers | Thermotropic liquid crystalline polymers; Polycarbonates Boric acid |
| Styrene-acrylic copolymers (e.g. poly(styrene-co-N-dimethylaminoethyl methacrylate)) | Hydroquinone; Diaminophenylene |
| Polyolefins | Norbornene functionalized polymers Pour-point depressants for paraffinic hydrocarbon oils such as unsaturated ester polymers and/or copolymers described in U.S. Pat. No. 4110283; U.S. Pat. No. 4663471; and U.S. Pat. No. 4762946 Oligomer hydrocarbon resins |

As a general rule, to which exceptions occur, organic nucleating agents should have these attributes:

Crystal structure should be similar to that of the polymer. Increasing compatibility of crystal structure promotes crystal growth;

Nucleating agent should be insoluble in the polymer;

Melting point of nucleating agent should be above the melting point of the polymer;

Nucleating agent should be non-volatile and inert towards environment (polymer, oxygen, humidity, other additives, etc.); and Nucleating agent should be well-dispersed in the polymer.

Table 2 provides examples of various types of polymers and crystallization enhancers which may be utilized therewith:

TABLE 2

| Polymer | Enhancers |
| --- | --- |
| Polyolefins | Organic or mineral nucleating agents, such as 1,2,3,4-bis-(3,4-dimethylbenzylidene sorbitol), methyldibenzylidene sorbitol, calcium stearate, Irgaclear ® D, Irgaclear ® DM, Irgaclear ® B 215, Milad ® 3988 |
| Polyesters and polyester block copolymers | Diphenylketone Eu(acac)$_3$.diPy Mn(CH$_3$COO)$_2$ + SbO$_3$ Selar ® resins (PET polyolefin blends) |
| Polyamides; Poly(amide-ether) block copolymers; Poly(amide-ether-ester) block copolymers | Polyamide/(acrylonitrile-butadiene-styrene terpolymer) Polyamide/(styrene-acrylonitrile copolymer) |

Table 3 provides citations to examples of nucleating agents for polymer materials which occur in the open literature.

TABLE 3

| nucleating agent | polymer | reference | year | vol | no | page(s) |
|---|---|---|---|---|---|---|
| 1,2,3,4-bis-(3,4-dimethylbenzylidene sorbitol) | polypropylene (PP) | Journal of Applied Polymer Science | 2002 | 84 | | 2440-2450 |
| 1,3:2,4-Bis-(m-methylbenzylidene) sorbitol | polypropylene (PP) | Macromolecular Symposium | 2001 | 176 | | 63-91 |
| calcium stearate | polypropylene (PP) | Macromolecular Symposium | 2001 | 176 | | 83-91 |
| CrO3/SiO2/Sl | polyethylene | Macromolecules | 1999 | 32 | | 8910-8913 |
| diphenylketone | crystalline copolymers based on poly(ethylerte terephthalate) | Journal of Applied Polymer Science | 2001 | 79 | | 497-503 |
| Eu(acac)3.diPy | poly(ethylene terephthalate) | Polymer | 1997 | 38 | 17 | 4469-4476 |
| Irgaclear ® D | polypropylene (PP) | Macromolecular Symposium | 2001 | 176 | | 83-91 |
| Irgaclear ® OM | polypropylene (PP) | Macromolecular Symposium | 2001 | 176 | | 83-91 |
| Irganox ® B 215 (Irgafos ® 168:Irganox ® 1010 = 2:1) | polypropylene (PP) | Macromolecular Symposium | 2001 | 176 | | 83-91 |
| liquid crystalline polymer | maleic anhydride-grafted polypropylene (m-PP) | Journal of Applied Polymer Science | 1996 | 64 | | 707-715 |
| methyldibenzylidene sorbitol | polypropylene (PP) | Journal of Applied Polymer Science | 2002 | 84 | | 2440-2450 |
| Millad 3988 | polypropylene (PP) | Macromolecular Symposium | 2001 | 176 | | 83-91 |
| Mn(CH3COO)2 + Sb2O3 | poly(ethylene terephthalate) | Polymer | 1997 | 38 | 17 | 4469-4476 |
| PA6/acrylonitrile-butadiene-styrene terpolymer (ABS) | polyamide 6 (PA6) | Journal of Applied Polymer Science | 2002 | 84 | | 2753-2759 |
| PA6/styrene-acrylonitrile copolymer (SAN) | polyamide 6 (PA6) | Journal of Applied Polymer Science | 2002 | 84 | | 2753-2759 |
| poly(L-lactide) (PLLA) | poly(L-lactide) poly(D-lactide) stereocomplex | Journal of Polymer Science: Part B: Polymer Physics | 2001 | 39 | | 300-313 |
| residual metatlocence catalysts | syndiotactic Polypropylene (sPP) | Journal of Applied Polymer Science | 2000 | 75 | | 337-346 |
| Sm(CH3COO)3•xH2O | poly(ethylene terephthalate) | Polymer | 1997 | 38 | 17 | 4469-4476 |
| sodium acetate | crystalline copolymers based on poly(ethylene terephthalate) | Journal of Applied Polymer Science | 2001 | 79 | | 497-503 |
| sodium benzoate | crystalline copolymers based on poly(ethylene terephthalate) | Journal of Applied Polymer Science | 2001 | 79 | | 497-503 |
| sodium benzoate | nylon | Makromoleciile Band 1 + 2 Technologie, 5th Edition | 1994 | | | 34 |
| sodium benzoate | polypropylene (PP) | Makromolec0le Band 1 + 2 Technologie, 5th Edition | 1994 | | | 34 |
| sodium stearate | glass-filled poly(propylene terephthalate) (GF PPT) | Journal of Applied Polymer Science | 1999 | 74 | | 889-899 |
| styrene-acrylonitrile-maleic anhydride copolymer (SAN MA) | polyamide 6 (PA6) | Journal of Applied Polymer Science | 2002 | 84 | | 2753-2759 |
| substituted sorbitol acetals | polypropylene (PP) | Journal Polymer Science, Polymer Letters | 1983 | 21 | | 34 |
| substituted sorbitol acetals | polypropylene (PP) | Macromolecular Symposium | 2001 | 176 | | 83-91 |
| substituted sorbitol acetals | polypropylene (PP) | Progress in Colloidial Polymer Science | 1992 | 87 | | 2 |
| talc | glass-filled poly(propylene terephthalate) (GF PPT) | Journal of Applied Polymer Science | 1999 | 74 | | 889-899 |
| talc | poly(L-lactide) poly(D-lactide) stereocomplex | Journal of Polymer Science: Part B: Polymer Physics | 2001 | 39 | | 300-313 |

TABLE 3-continued

| nucleating agent | polymer | reference | year | vol | no | page(s) |
|---|---|---|---|---|---|---|
| talc | polypropylene (PP) | Journal of Applied Polymer Science | 2002 | 84 | | 2440-2450 |
| talc & other mineral fillers | nylon | Kunsistoffe Aktuell | 1973 | 27 | | 10 |
| talc & other mineral fillers | PBT | Kunststoffe Aktuell | 1973 | 27 | | 10 |
| Tb(acac)3.diPy | poly(ethylene terephthalate) | Polymer | 1997 | 38 | 17 | 4469-4476 |
| Ti(Q-n-C4H9)4 | poly(ethylene terephthalate) | Polymer | 1997 | 38 | 17 | 4469-4476 |

A polymer system employing a crystallization inhibitor is described in U.S. Pat. No. 5,306,246 (Sahatjian) in which PET/polyolefin blends (Selar® resins) are added to PET in amounts up to 20% by weight of the composition.

Another polymer system employing a crystallization inhibitor is described in WO 94/21726 in which single-layer oriented heat-shrinkable films are obtained from polymer compositions comprising an ethylene/a-olefin copolymer, a polymeric alloy (made up of a heterophasic composition in which an amorphous ethylene/propylene copolymer is dispersed in a homopolymeric propylene matrix) and/or a random copolymer of propylene with ethylene, and a crystallization inhibitor For this purpose the crystallization inhibitor may be one or more of aliphatic and aromatic hydrocarbon resins, aliphatic and aromatic copolymers, such as polymers and copolymers of piperylene, methylbutene, isobutene, vinyltoluene, indene, α-methylstyrene, polycyclodiene, etc.; hydrogenated $C_9$ resins; and pinene and rosin resins and terpene resins.

Nucleating agents which may be employed in the compositions as crystallization enhancers are known, for instance from US 20030054161, US 20030148056, and U.S. Pat. No. 6,610,765. As reported in these documents nucleating agents which have been used previously for polymer films include mineral nucleating agents and organic nucleating agents. Examples of mineral nucleating agents include carbon black, silica, kaolin, sodium bicarbonate and talc. Among the organic nucleating agents which have been suggested as useful in polyolefin films include salts of aliphatic mono-basic or di-basic acids or arylalkyl acids such as sodium succinate, sodium glutarate, sodium caproate, sodium 4-methylvalerate, sodium-2-2'-methylenebis(4,6-di-tert-butylphenyl)phosphate, aluminum phenyl acetate, and sodium cinnamate. Alkali metal and aluminum salts of aromatic and alicyclic carboxylic acids such as aluminum benzoate, sodium or potassium benzoate, sodium beta-naphtholate, lithium benzoate and aluminum tertiary-butyl benzoate also are useful organic nucleating agents. The free acids of the above mentioned salts may also be suitable. Benzenesulfonamides have been reported to be useful nucleating agents, as well as substituted sorbitol derivatives such as bis-(benzylidene) and bis-(alkylbenzilidine) sorbitols wherein the alkyl groups contain from about four to about eighteen carbon atoms. Particular such substituted sorbitol derivatives are compounds of formula I

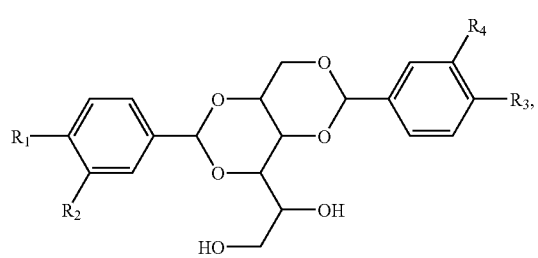

(I)

wherein $R_1$, $R_2$, $R_3$ and $R_4$ are each independently of one another hydrogen or $C_1$-$C_4$ alkyl, and $C_1$-$C_4$ alkyl is a branched or unbranched radical, for example methyl, ethyl, n-propyl, isopropyl, n-butyl, isobutyl or tert-butyl. Specific nucleating agents are the compounds of formula 1a (Irgaclear® DM), 1b (Irgaclear® D) and 1c (Millad® 3988).

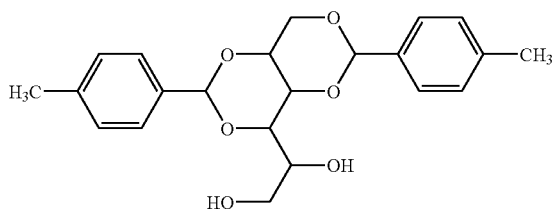

(Ia)

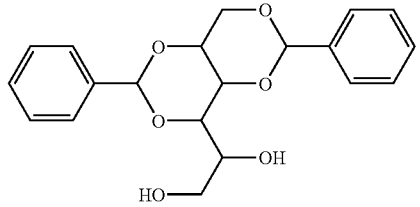

(Ib)

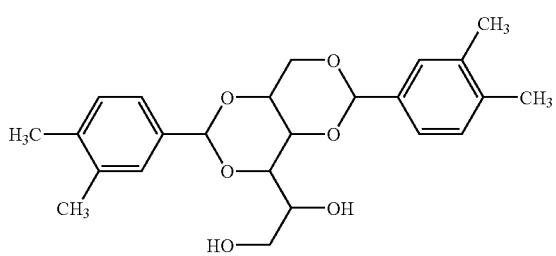

(Ic)

Irgaclear® DM and Irgaclear® D are registered trademarks of Ciba Spezialitatenchemie AG. Millad® 3988 is a registered trademark of Milliken & Company. Mixtures of any of the nucleating agents may be used, for instance a mixture of Irgaclear® DM and sodium benzoate. Other nucleating agents which can be used include phosphate ester based products such as NA-11 and NA-21 supplied by Asahi-Denka Kogyo of Japan, and a norbornane carboxylic acid salt based product HPN-68 supplied by Milliken & Company.

The nucleating agents described above are typically used with polyolefins, especially polypropylene polymers and copolymers, but in some polyethylene polymers or copolymers. Similar nucleating agents can be used for other semi-crystalline polymers.

The amounts of crystallization modifier incorporated into the formulations of the present invention will vary depending on their impact on the specific polymer employed in the composition and the degree of crystallization modification desired. In some cases quite small amounts, for instance as low as 100 ppm, may be suitable, especially in the case where the modifier is a nucleating agent, while in other cases amounts in excess of 3%, for instance up to 20% by weight may be suitable, particularity in the case of polymer or resinous crystallization inhibitors or up to 10% by weight in the case of nucleating agents. In some cases the maximum desirable amount will be in the range of from 0.1-1% by weight.

In accordance with the invention, varying the amount of the crystallization modifier by location within the inventive device part allows a more effective tailoring of properties of such part to localized differences in desired properties such as strength, softness, flexibility, distension and the like. The variation may be step-wise, or continuous, and it may range from zero to some positive amount, or between positive amounts. For example the modifier may be varied from zero to about 20% by weight of the polymer composition, from zero to about 10%, from 0.5% to about 5%, from 100 ppm to 2000 ppm, or from zero to about 3% by weight of the polymer composition.

A single medical device part may also be provided with more than one crystallization rate modifier. For instance a catheter inner shaft may be formed from a polymer composition comprising a crystallization rate enhancer in a proximal region, the enhancer tapering to zero moving distally. Then, at the distal end, a crystallization rate inhibitor may be incorporated into the composition. A polymer composition incorporating a crystallization enhancer may be used to form a catheter outer in the proximal region, the composition having a lesser or no amount of enhancer in an intermediate region and then once again incorporate an enhancer just proximal of the distal end to increase yield strength and thereby enhance resistance to necking during withdrawal of the catheter.

The composition variation employed in the invention can be coupled with concurrent complementary variations in extrusion or injection parameters which alter the available crystallization time, or device profile, to further increase the difference proximal to distal in stiffness, flexibility and/or other crystallization related physical properties. For instance a crystallization enhancer may be incorporated into an extrusion melt at the same time that the tank gap is changed to enhance longitudinal orientation and/or the tube diameter or wall thickness is increased. Crystalline structure in the formed part stabilizes polymer orientation obtained from processing operations such as extrusion, stretching, and parison blow-forming techniques, reducing creep relaxation which may occur over time or as a result of use stress.

Where the desired locality of the modified composition is small, extrusion and injection systems which allow changeover from one composition to another using very low volumes are preferably used. Where a gradual transition in properties is desired a wider range of composition supply systems can be used. Co-injection molding, gradient extrusion, coextrusion, and intermittent extrusion equipment are examples of supply systems which may be used.

The invention has application to the preparation of preformed balloon parisons, for instance providing a crystallization inhibitor in the distal and/or proximal waist region to reduce crystallization during laser welding of the balloon to the catheter. Concurrently, or alternatively, in the portion of the parison used to form balloon body region a crystallization enhancer may be employed to reduce creep behavior and enhance the elastic response of the balloon after a first inflation.

In a multi-layer laminate catheter or balloon, crystallization modifiers may be employed in one or multiple layers. This may be desirable, for instance, to increase or decrease selected property differences between the two layers.

Referring to the figures, FIG. 1 shows an extruded balloon parison 10 prepared in accordance with an aspect of the invention, with crosshatching indicating the variation in composition. The segment has three distinct regions 1, 2, 3, each with different levels of crystallization. Region 3 has a crystallization inhibitor incorporated into the polymer composition and will produce a balloon waist portion which undergoes very little crystallization as a consequence of heat bonding to the catheter distal tip. Region 2 is a transition region as the composition changes over to an unmodified polymer composition in region 1. In subsequent processing operations region 1 will form the balloon body, region 2, will form the proximal cone, or a distal portion thereof, and region 3 will form a waist portion of the balloon.

A balloon having some crystallization inhibitor in the cone region may be desirable, for instance, to improve re-inflation cycle integrity of balloons which are heat set. Heat setting, at a temperature above the blowing temperature, increases polymer crystallization after the balloon is initially formed. Heat setting increases balloon inflation strength, but can reduce ability of the balloon to under go repeated inflations to dilatation pressures without failure. Failure in the cone regions has been observed. Using a crystallization inhibitor in the cone region but not in the balloon body portion, when forming a heat set balloon, can allow the increased burst strength advantages of heat set balloons to be retained while the disadvantage of reduced re-inflation cycle integrity is minimized or eliminated.

More complex patterns are also available. Stepped transitions may be produced, stepping progressively up or down, or both up and down in crystallization modifier, the length of transition region(s) may be different for different steps, or the variation in composition may be continuous. For instance using a single polymer, continuous variation of modifier component of the polymer composition over an elongated region of a catheter shaft may displace the need to manufacture the shaft in two or more segments of different polymers.

Figure 2:
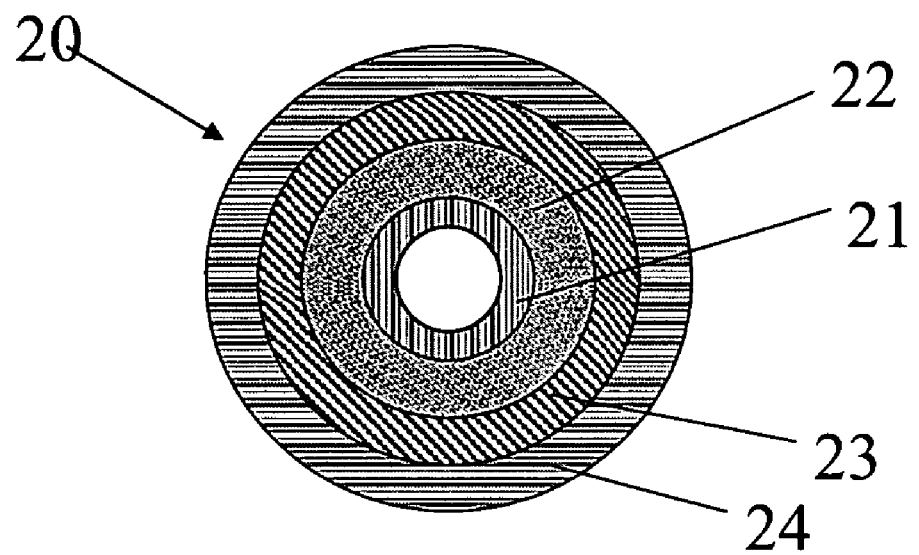
FIG. 2 is a cross-sectional view of a tubular member in which the polymer composition is varied step-wise through the thickness dimension, in accordance with another embodiment of the invention.

In a multi-layer laminate catheter or balloon a crystallization modifier may be employed to increase property differences in the two layers. FIG. 2 shows a cross-sectional view of a multi-layer tube 20 which is formed of layers 21, 22, 23, and 24 which may all be formed of the same polymer, but differing polymer compositions due to the presence and/or amount of crystallization inhibitor or enhancer. The crystallinity variation may step up or down linearly as one passes through the thickness dimension of the tube, it may alternate between layers of lower crystallization and higher crystallization, or it may follow some other pattern.

Figure 3:
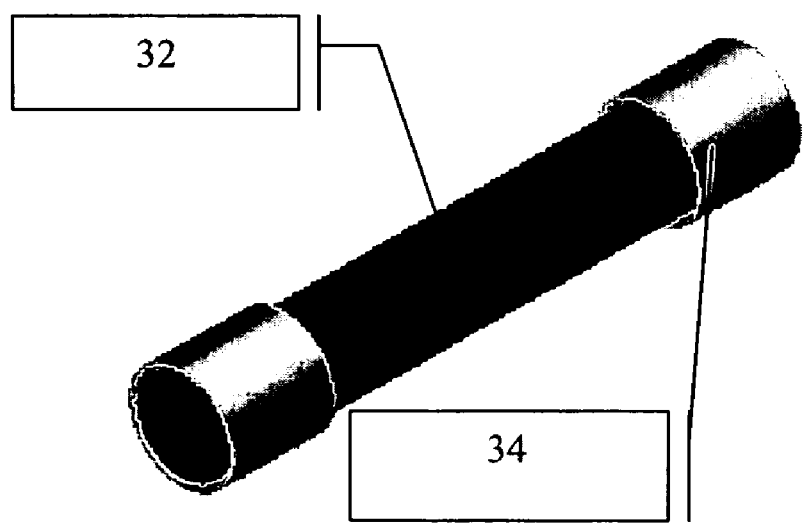
FIG. 3 is a perspective view of a tubular balloon parison prepared in accordance with a still further embodiment of the invention.

FIG. 3 depicts a tube 32, which may be, for instance a catheter tube segment 32, or a balloon parison. Tube 32 includes layer 34 deposited by an intermittent extrusion, in selected regions. Layer 34 may be substantially the same polymer material as the underlying tube, except that it is provided with a crystallization modifier. For instance in the case of a catheter tube, the layer may be a crystallization inhibitor, deposited at fusion bonding sites, such as where the balloon is bonded to the shaft, so as to reduce crystallization, and resulting stiffening at those sites as a result of the fusion bonding step.

Differences in polymer modulus of as much as four times may be produced, relative to unmodified polymer, simply by the incorporation of an optimal amount of a crystallization inhibitor or enhancer. Even larger differences may be obtainable if the composition transitions from incorporation of an enhancer in one portion of the device to an inhibitor in another portion.

In a catheter shaft application, selective crystallization and tube wall reduction could enable a continuous tapered shaft from one material without the need for distal shaft bonds. This can be coupled with concurrent complementary variations in extrusion parameters which alter the available crystallization time, to further increase the difference proximal to distal in stiffness, flexibility and/or other crystallization related physical properties.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims).

The invention claimed is:

1. A a dilatation balloon, formed of a polymer material composition, the polymer material composition comprising at least one crystallizable base polymer and, in at least a portion of the part, further comprising a crystallization modifier, wherein
from a first portion of the balloon to a second portion of the balloon, the polymer material composition, is varied in amount of crystallization modifier relative to the amount of said at least one crystallizable base polymer.

2. A a dilatation balloon as in claim 1 wherein said crystallization modifier amount is varied within the range of from 0 to about 20 percent by weight of the polymer composition.

3. A a dilatation balloon as in claim 1 wherein said crystallization modifier enhances crystallization of said base polymer.

4. A a dilatation balloon as in claim 1 wherein said crystallizable base polymer is selected from the group consisting of olefin, acrylic, styrenic and vinyl polymers and copolymers; polyethers; polyamides; polycarbonates; polyesters; polyurethanes; thermoplastic polyimides; liquid crystal polymers; ABS (acrylonitrile butadiene styrene); ANS (acrylonitrile styrene); polyacetal; PEI (polyetherimide); polyetheretherketone (PEEK); and polyether sulfone (PES); block copolymers comprising at least one polyolefin, polyacrylic, polystyrenic, polyvinyl, polyether, polyamide, polyester, or polyurethane block therein, and mixtures of any of said polymers.

5. A dilatation balloon as in claim 1 wherein the crystallization modifier is a crystallization inhibitor.

6. A dilatation balloon as in claim 5 comprising a balloon body portion and proximal and distal waist portions, wherein the crystallization modifier is present in the distal waist portion of the device.

7. A dilatation balloon as in claim 6 wherein the crystallization modifier is not present in the balloon body portion of the device.

8. A catheter balloon formed of a polymer material composition, the polymer material composition comprising at least one crystallizable base polymer which is partially crystallized over at least a portion of the balloon length or thickness or both, wherein the polymer material composition includes at least one crystallization modifier which varies in concentration over a portion oft he balloon, and the degree of crystallization of said crystallizable base polymer, taken as a fraction thereof, varies over said portion.

9. A catheter balloon as in claim 8 wherein the balloon comprises a body portion, the body portion located between opposed cone portions, the cone portions, respectively, located between opposed waist portions by which the balloon may be attached to a catheter and wherein the degree of crystallization in the waist portions is less than in the body portion.

10. A catheter balloon as in claim 9 wherein the degree of crystallization in the cone portions is less than in the body portion and greater than in the waist portions.

11. A catheter balloon as in claim 8 wherein the crystallization modifier comprises a crystallization enhancer.

12. A catheter balloon as in claim 11 wherein the crystallization enhancer is a nucleating agent.

13. A catheter balloon as in claim 12 wherein the nucleating agent is a member of the group consisting of carbon black, silica, kaolin, sodium bicarbonate, talc, sodium succinate, sodium glutarate, sodium caproate, sodium 4-methylvalerate, sodium-2-2'-methylenebis(4,6-di-tert-butylphenyl)phosphate, aluminum phenyl acetate, sodium cinnamate, alkali metal and aluminum salts of aromatic and alicyclic carboxylic acids, benzoic acid, naphthoic acid, tertiary-butyl benzoic acid, benzenesulfonamides, bis-(benzylidene) sorbitols, bis-(alkylbenzilidine) sorbitols, phosphate esters, norbomane carboxylic acid salts, and mixtures thereof.

14. A catheter balloon as in claim 8 wherein the crystallization modifier comprises a crystallization inhibitor.

15. A catheter balloon as in claim 14 wherein the crystallization inhibitor is a compound which ties up nucleating sites or terminates crystal 16. A catheter balloon as in claim 14 wherein the crystallization inhibitor comprises a member of the group consisting of polymers and copolymers of piperylene, methylbutene, isobutene, vinyltoluene, indene, α-methylstyrene, or polycyclodiene; hydrogenated $C_9$ resins; pinene resins; rosin resins; terpene resins, lithium (bis)trifluoromethanesulfonate imide.

17. A catheter balloon as in claim 8 wherein said crystallizable base polymer is selected from the group consisting of olefin, acrylic, styrenic and vinyl polymers and copolymers; polyethers; polyamides; polycarbonates; polyesters; polyurethanes; thermoplastic polyimides; liquid crystal polymers; ABS (acrylonitrile butadiene styrene); ANS (acrylonitrile styrene); polyacetal; PEI (polyetherimide); polyetheretherketone (PEEK); and polyether sulfone (PES); block copolymers comprising at least one polyolefin, polyacrylic, polystyrenic, polyvinyl, polyether, polyamide, polyester, or polyurethane block therein, and mixtures of any of said polymers.

18. A catheter balloon as in claim 17 wherein said crystallizable base polymer comprises a polyamide/polyether block copolymer or polyester/polyether segmented block copolymer.

19. A catheter balloon as in claim 17 wherein said crystallizable base polymer comprises a liquid crystal polymer.

20. A catheter balloon as in claim 8 wherein the one crystallization modifier varies in concentration in the polymer material composition through the thickness of the balloon.

21. A catheter balloon as in claim 8 wherein the one crystallization modifier varies in concentration in the polymer material composition along the length of the balloon.

* * * * *